United States Patent [19]

Hayes

[11] Patent Number: 5,674,193
[45] Date of Patent: Oct. 7, 1997

[54] ORAL/NASAL-GASTRIC DRAINAGE KIT

[76] Inventor: Lili L. Hayes, 8420 Galley Ct., Indianapolis, Ind. 46236

[21] Appl. No.: 417,093

[22] Filed: Apr. 5, 1995

[51] Int. Cl.⁶ .................................................. A61M 1/00
[52] U.S. Cl. ............................. 604/28; 604/30; 604/236; 604/248
[58] Field of Search ....................... 604/43, 45, 128, 604/284, 236, 248, 250, 183, 270, 30, 35, 36, 28, 49, 150; 128/768

[56] References Cited

U.S. PATENT DOCUMENTS

| | | | |
|---|---|---|---|
| 1,847,954 | 3/1932 | Fisher | 604/30 |
| 2,078,180 | 4/1937 | Kronenberg | 604/30 |
| 2,860,636 | 11/1958 | Seitchik et al. | 604/35 |
| 3,048,192 | 8/1962 | Murphy, Jr. | 604/248 |
| 3,316,910 | 5/1967 | Davis | 604/30 |
| 4,902,282 | 2/1990 | Bellotti et al. | 604/258 |
| 5,256,139 | 10/1993 | Ghodsian | 604/49 |
| 5,269,768 | 12/1993 | Cheung | 604/248 |

*Primary Examiner*—Vanitha M. Alexander
*Attorney, Agent, or Firm*—Barnes & Thornburg

[57] ABSTRACT

The present invention provides a method and device for draining gastric fluid from a patient. An oral/nasal-gastric tube is provided which includes a gastric inlet, a suction outlet formed for attachment with a suction-drain collection container, a bypass outlet formed for attachment with a gravity-drain collection container, and at least one valve positioned on the oral/nasal-gastric tube. An optional clearance tube is provided for extension between the gravity-drain collection container and the suction-drain collection container so that fluids may be drained, cleared to the collection canister and then may be easily disposed.

7 Claims, 2 Drawing Sheets

ORAL/NASAL-GASTRIC DRAINAGE KIT

The present invention relates to the draining of gastric fluid from a patient. More particularly, the present invention is directed to a device and method for emptying gastric fluid from a patient during surgery.

Oral/nasal-gastric devices designed for insertion through an oral/nasal passageway and into the digestive tract are commonly used in medical treatment. Such oral/nasal-gastric devices are used for removing fluid from the gastro-intestinal tract during the performance of diagnostic testing or surgery. Typically, such oral/nasal-gastric devices include a flexible line or tube having one end positioned within the stomach and the opposite end attached to a conventional suction-drain collection container.

Generally, oral/nasal-gastric devices operate by way of a suction pump which creates a vacuum to pull the gastric fluid through the line and into the suction-drain collection container. The vacuum is applied on an intermittent basis for the entirety of the procedure to ensure that additional fluid which has been produced within the stomach is removed. However, when fluid is forcibly suctioned from the patient for a lengthy period of time, the lining of the stomach may become irritated. This irritation is especially noted in patients who are conscious during the surgical procedure or testing. For these and other reasons, improved techniques for removing fluid from the gastro-intestinal tract are needed.

The present invention is directed accordingly to an oral/nasal-gastric drainage kit for use in combination with a conventional suction-drain collection container in removing fluid from the gastro-intestinal tract of a patient. The use of this oral/nasal-gastric drainage kit will reduce the occurrence of stomach irritation. The kit in accordance with the present invention comprises a flexible tube having a gastric inlet formed for insertion into the stomach, a suction outlet formed for communication with a suction-drain collection container, a bypass outlet formed for communication with a gravity-drain collection container, and at least one valve positioned on the tube. The manipulation of at least one valve selectively blocks a suction passageway and/or a bypass passageway extending between the gastric inlet and the suction and bypass outlets respectively.

The kit preferably includes the gravity-drain collection container. Ideally, a clearance tube for gravity bag clearance formed for extension between the gravity-drain collection container and the suction-drain collection container may be provided. This clearance tube is to permit fluid which has drained into the gravity-drain collection container to be suctioned into the collection container for easy disposal.

The present invention is further directed to a method for reducing or eliminating irritation of the stomach during removal of gastric fluid. The method comprises providing an oral/nasal-gastric drainage tube having a gastric inlet, a suction outlet formed for attachment with a suction-drain collection container, a bypass outlet formed for attachment with a gravity-drain collection container, and at least one valve positioned on the oral/nasal-gastric tube. The gastric inlet is inserted through the oral or nasal passageway and into the stomach of the patient. After the suction and bypass outlets are attached to their respective containers, at least one valve is manipulated to allow the suction pump to pull fluid present within the stomach of the patient through the gastric inlet and into the suction-drain collection container. The suction pump pulls fluid through the oral/nasal-gastric drainage tube in this manner for generally 10 to 15 seconds to substantially clear the stomach of gastric fluid.

Once the stomach is substantially free of fluid, at least one valve is adjusted to cut-off the suction pump from the gastric inlet and to allow additional fluid present within the stomach to naturally drain through the bypass outlet and into the gravity-drain collection container. Fluid may be allowed to naturally drain through the bypass outlet until the end of the procedure. Preferably, a clearance tube is provided for extension between the gravity-drain collection container and the suction-drain collection container. Thus, fluid positioned within the gravity-drain collection container may be evacuated into the suction-drain collection container for easy disposal.

Other objects and features of the present invention will become apparent as this description progresses.

DETAILED DESCRIPTION OF THE INVENTION

Figure 1:
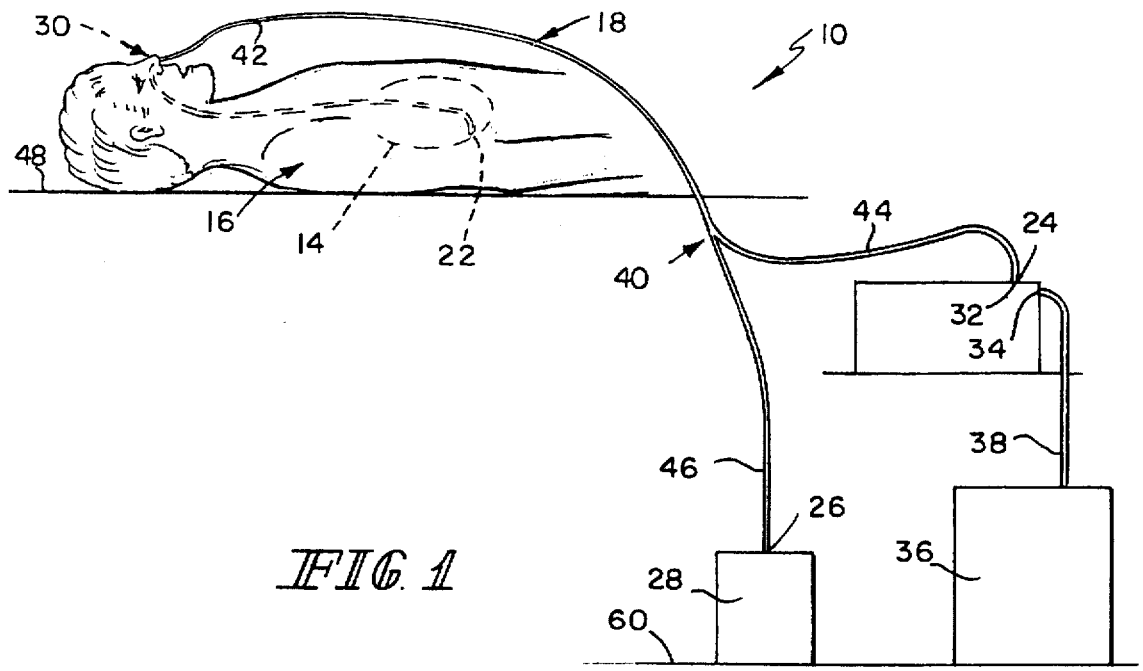
FIG. 1 is a schematic representation illustrating use of an oral/nasal-gastric drainage kit in accordance with the present invention and showing an oral/nasal-gastric tube having a gastric inlet positioned in a stomach, a suction outlet coupled to a suction-drain collection container and a bypass outlet coupled to a gravity-drain collection container.
Figure 2:
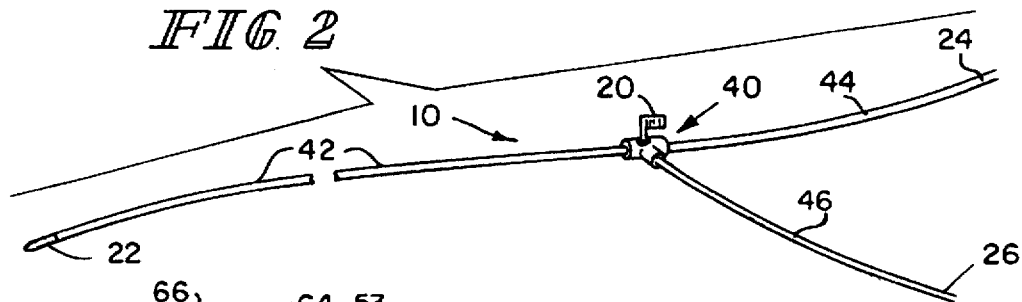
FIG. 2 is a perspective view of the oral/nasal-gastric tube of FIG. 1 and showing a junction, a valve positioned at the junction, and gastric, suction, and bypass portions extending radially outwardly from the junction.
Figure 3:
FIG. 3. is an enlarged sectional view of the junction of FIG. 2 and showing the valve positioned in an first suction position, a suction passageway extending through the suction portion of the tube and a bypass passageway extending through the bypass portion of the tube.
Figures 4, 5:
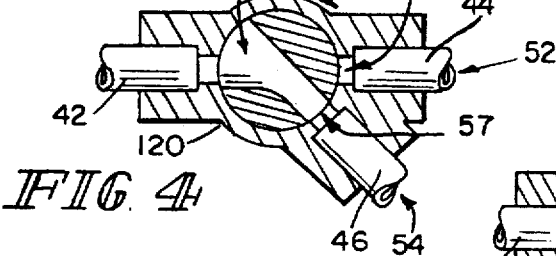
FIG. 4 is an enlarged sectional view of the junction of FIG. 3 and showing the valve positioned in a second drain position so that fluid flows from the gastric portion into the bypass portion of the oral/nasal-gastric tube.
FIG. 5 is an enlarged sectional view of the junction of FIG. 3 and showing the valve positioned in a closed position so that fluid is prevented from flowing from the gastric portion into either the suction portion or the bypass portion of the oral/nasal-gastric tube.

An oral/nasal-gastric drainage kit 10 and method in accordance with the present invention operates in combination with a conventional suction-drain collection container 12 to reduce irritation to a stomach 14 while draining gastric fluid (not shown) from a patient 16. The oral/nasal-gastric drainage kit 10 is shown in FIG. 1 as it would appear after it has been inserted into the patient 16. Kit 10 comprises an oral/nasal-gastric tube 18 and at least one valve 20 (see FIGS. 2–5) positioned on the tube 18. Illustratively, the oral/nasal-gastric tube 18 has a gastric inlet 22 formed for insertion into the stomach 14 of the patient 16, a suction outlet 24 formed for communication with the suction-drain collection container 12, and a bypass outlet 26 formed for communication with a gravity-drain collection container 28.

The suction outlet 24 of the oral/nasal-gastric tube 18 is formed to be securely attached to a wide variety of suction-drain collection containers 12 configured for attachment to conventional "oral/nasal-gastric lines" (not shown). The term "oral/nasal-gastric line" as used herein is meant any medical-instrument associated tube adapted for insertion into the stomach 14 of the patient 16 to drain fluid therefrom with the help of suction. The well known suction-drain collection container 12 is designed to hold fluid pulled from the stomach 14 and includes an oral/nasal-gastric line inlet 32 and a connector-line inlet 34. Preferably, the container 12 is disposable so that the caregiver may easily discard the fluid following each procedure.

Additionally, the well known suction-drain collection container 12 communicates with a suction pump 36 by a connector tube 38 which extends between the connector-line inlet 34 and the pump 36. The suction pump 36 may therefore create a vacuum within the suction-drain collection container 12 and the oral/nasal-gastric tube 18 to pull fluid out of the patient 16. Most operating rooms are equipped with suction pumps or suction lines connected to common suction pump arrangements. It will be appreciated that the pump 36 may be any of a wide variety of pump and suction line arrangements which do not need to be described herein. It will also be appreciated that the level and amount of suction used for oral/nasal-gastric lines in widely known by medical personnel and need not be discussed herein.

The oral/nasal-gastric tube 18 includes a junction 40 therein which is formed to be positioned vertically below the gastric inlet 22. See FIG. 1. The oral/nasal-gastric tube 18 illustratively includes a gastric portion 42, a suction portion 44, and a bypass portion 46 extending outwardly from the junction 40. The gastric portion 42 extends between the junction 40 and the gastric inlet 22, the suction portion 44 extends between the junction 40 and the suction outlet 24, and the bypass portion 46 extends between the junction 40 and the bypass outlet 26. The oral/nasal-gastric tube 18 may be Y-shaped in appearance and is constructed of flexible polymeric materials which allow it to follow contours in either a oral passageway (not shown) or a nasal passageway 30 and about a surgical table 48. Generally, the diameter of the oral/nasal-gastric tube 18 ranges from 16 to about 24 French and the tube 18 is about 20 inches in length. However, the diameter and length of the oral/nasal-gastric tube 18 may vary greatly depending upon the size of the patient 16 and of the medical facilities.

Illustratively, a valve 20 may be positioned on the oral/nasal-gastric tube 18. See FIG. 2. It is contemplated that the valve 20 may be selected from a wide range of commercially available valves. Thus the valve 20 of the present invention can be selected from gate valves, two-way directional valves, three-way directional valves, sliding valves, pinch valves, and rotating valves. For instance, valve 20 may be a directional valve 120. See FIG. 3. Directional valve 120 includes a first suction position 50. A suction passageway 52 extending through the suction portion 44 between the junction 40 and the suction outlet 24 is placed in an open position 53 when the valve 120 is in the first suction position 50.

Additionally, directional valve 120 includes a bypass passageway 54 through the bypass portion 46 between the junction 40 and the bypass outlet 26. Illustratively, the bypass passageway 54 is in a closed position 55 between the junction 40 and the bypass outlet 26 in first suction position 50, but is in an open position 57 following movement of the directional valve 120 to either a second drain position 58 or a closed position 56. See FIGS. 4 and 5. When valve 120 is in the closed position 56, the first suction passageway 52 is in a closed position 59 between the junction 40 and the suction outlet 24 and the second bypass passageway 54 is in the open position 57. Both passageways 52, 54, however, are effectively blocked from the gastric portion 42 of the oral/nasal-gastric tube 18.

Figure 6:
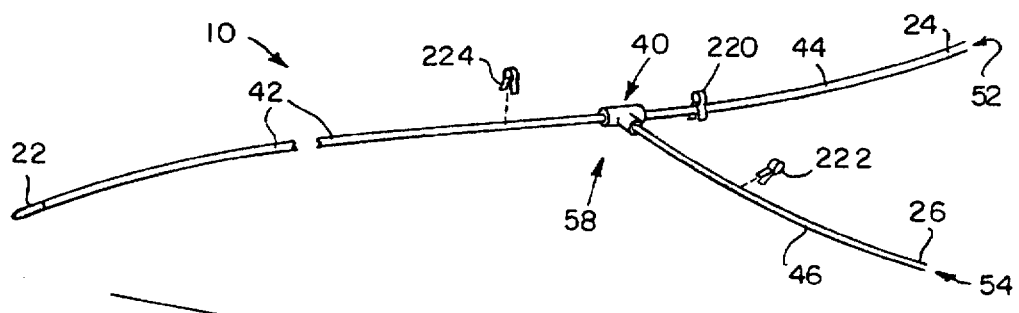
FIG. 6 is a perspective view of an alternative embodiment of the tube of FIG. 2 and showing the valve being three adjustable pinch valves formed for clamping the suction portion, the gastric portion, and the bypass portion of the oral/nasal-gastric tube in order to direct the flow of fluid.

It is contemplated that valve 20 of the kit 10 may comprise a variety of well known adjustable pinch valves 220, 222, 224 positioned on the oral/nasal-gastric tube 18 to either serve as directional flow regulators or to clamp-off a portion 42, 44, 46 of the tubing. See FIG. 6. For example, a first pinch valve 220 may be positioned on the suction portion 44 to block the first suction passageway 52 between the suction outlet 24 and the junction 40. When pinch valve 220 closes the first suction passageway 52, the oral/nasal-gastric tube 18 is effectively in the second drain position 58. Additionally, pinch valve 222 may be positioned on the bypass portion 46 and pinch valve 224 may be positioned on the gastric portion 42. Adjustment of the positioning of pinch valves 220, 222, 224 guides the flow of fluid through the oral/nasal-gastric tube 18.

Preferably, the gravity-drain collection container 28 is provided with kit 10. The gravity-drain collection container 28 is formed to be positioned vertically below the gastric inlet 22 of the oral/nasal-gastric tube 18. See FIG. 1. Ideally, the patient 16 rests on the table 48 and the gravity-drain collection container 28 sits on a floor 60 beneath the table 48. It is contemplated that the gravity-drain collection container 28 may be selected from a wide variety of commercially available fluid collection containers. Thus, the gravity-drain collection container 28 may be selected from plastic containers, glass bottles, metal cans, and fluid container bags such as Foley bags.

Figure 7:
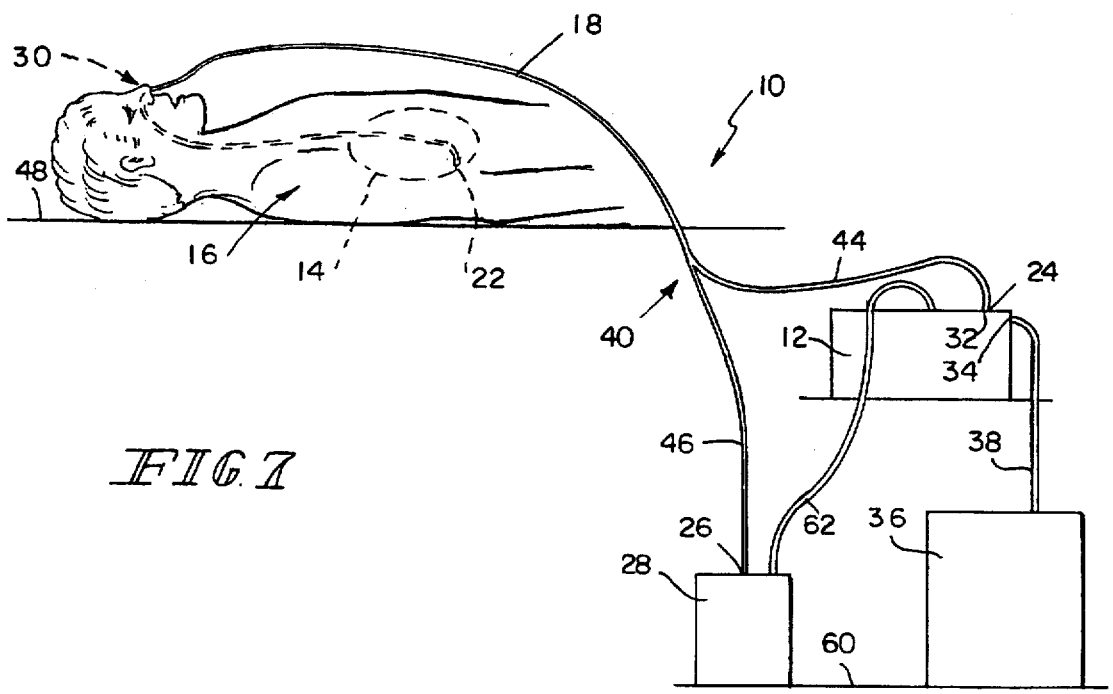
FIG. 7 is a schematic representation illustrating use of a modified oral/nasal-gastric drainage device in accordance with the present invention and showing the device having a clearance tube extending from a gravity-drain collection container to a suction-drain collection container.

Preferably, kit 10 also includes a clearance tube 62 extending between the gravity-drain collection container 28 and the suction-drain collection container 12. See FIG. 7. Illustratively, the clearance tube 62 is constructed of flexible polymeric materials which allow the tube 62 to flex and bend around corners of the surgical table 48 and equipment and into the suction-drain collection container 12. It is contemplated that an additional valve (not shown) may be positioned on the clearance tube 62 to selectively block suction into the gravity-drain collection container 28.

In practice of the method of the present invention, the oral/nasal-gastric tube 18 having the gastric portion 42, the suction portion 44, the bypass portion 46, and at least one valve 20 is provided. Illustratively, the gastric-inlet 22 of the gastric portion 42 is inserted through either the oral passageway (not shown) or nasal passageway 30 and into the stomach 14 of the patient 16. The suction outlet 24 of the oral/nasal-gastric tube 18 is attached to the gastric-line input 32 of the suction-drain collection container 12 and the bypass outlet 26 of the oral/nasal-gastric tube 18 is attached to the gravity-drain collection container 28. The valve 20 is initially manipulated to the first suction position 50. See for example the directional valve 120 in FIG. 3. Thus, the suction pump 36 pulls stomach fluid (not shown) through the first suction passageway 52 of the oral/nasal-gastric tube 18 and into the suction-drain collection container 12 for disposal. Substantially all of the fluid is emptied from the stomach 14 in this manner in about 10 to 15 seconds.

After the fluid has been evacuated from the stomach 14, the valve 120 is adjusted as shown by arrow 64 to a second drain position 58 to place the bypass passageway 54 in the open position 57. See FIG. 4. Thus, the suction portion 44 of the tube 18 is in the closed position 59 and the pump 36 is unable to suction fluid through the gastric tube 18. Note, the gravity-drain collection container 28 must be positioned vertically below the gastric inlet 22 to effectuate siphoning action of the fluid. Preferably, the patient 16 is positioned on the table 48 and the gravity-drain collection container 28 is located on the floor 60 beneath the table 48 and out of the path of the caregiver. See FIG. 1. Once the valve 120 is adjusted according to arrow 64 to separate the suction pump 36 from the gastric inlet 22 of the tube 18, fluid naturally drains into the second bypass passageway 54 in the bypass portion 46 where it empties into the gravity-drain collection container 28. Fluid continues to drain from the stomach 14 in this manner for the entirety of the procedure.

Additionally, in the method in accordance with the present invention the valve 120 is manipulated as shown by arrow 66 to the closed position 56 from the first suction position 50. See FIGS. 3 and 5. However, the valve 120 can also be moved to the closed position 56 from the second drain position 58 as shown by arrow 67. See FIG. 4. Thus, fluid present in the stomach 14 neither flows into the suction passageway 52 nor into the bypass passageway 54 of the oral/nasal-gastric tube 18. Preferably, the caregiver may turn the valve 120 as shown by arrow 68 to an evacuation position (not shown). In the evacuation position (not shown) the suction passageway 52 and the bypass passageway 54 are in communication with one another at the junction 40. Thus, the suction pump 36 pulls fluid positioned within the gravity-drain collection container 28 up through the bypass and suction portions 46, 44 and into the suction-drain collection container 12 for disposal.

Additionally, the method in accordance with the present invention includes the step of providing a clearance tube 62 which extends between the gravity-drain collection container 28 and the suction-drain collection container 12. See FIG. 7. At least one valve 20 is manipulated so that the first suction passageway 52 and the second bypass passageway 54 are in their closed positions 59, 57. Thus, fluid which has drained into the gravity-drain collection container 28 is removed into the suction-drain collection container 12 by the suction pump 36. This configuration allows the caregiver to easily evacuate the gravity-drain collection container 28.

Alternatively, the initial manipulation step of the method in accordance with the present invention may include the step of pinching closed the bypass passageway 54 with pinch valve 222 while fluid is pulled through the suction passageway 52 of the suction portion 44 of the oral/nasal-gastric tube 18. Likewise, the adjusting step may include releasing pinch valve 222 and pinching closed the suction passageway 52 with pinch valve 220 to siphon fluid through the bypass passageway 54 and into the gravity-drain collection container 28. It is contemplated, however, that the third pinch valve 224 may pinch the gastric portion 42 closed so that the suction pump 36 pulls fluid within the gravity-drain collection container 28 up through and the bypass portion 46 and suction portion 44 and into the suction-drain collection container 12.

Although the invention has been described in detail with reference to certain preferred embodiments, variations and modifications exist within the scope and spirit of the invention as described and defined in the following claims.

What is claimed is:

1. A method for reducing irritation of a stomach of a patient during medical and surgical procedures, the method comprising the steps of providing an oral/nasal-gastric drainage tube having a gastric inlet, a suction outlet formed for attachment with a suction-drain collection container, a bypass outlet formed for attachment with a gravity-drain collection container, and a valve positioned on the tube, inserting the gastric inlet through an oral/nasal passageway and into the stomach, manipulating the valve so that fluid produced in the stomach flows into the gastric inlet, through the suction outlet, and into the suction-drain collection container, and adjusting the valve so that the fluid flows through the bypass outlet and into the gravity-drain collection container, thereby removing the suction from the stomach.

2. The method of claim 1, wherein the fluid flows through the suction outlet for about 10 to about 15 seconds.

3. The method of claim 1, wherein the valve is a pinch valve and the adjusting step includes the step of pinching the tube so that the fluid flows only through the bypass outlet.

4. The method of claim 1, wherein the valve is a directional valve having a first suction position and a second drain position and the manipulating step includes the step of moving the valve to the first suction position.

5. The method of claim 4, wherein the adjusting step includes the step of moving the directional valve from the first suction position to the second drain position.

6. The method of claim 1, wherein the providing step includes the step of furnishing a clearance tube which is formed to extend between the gravity-drain collection container and the suction-drain collection container.

7. The method of claim 6, further comprising the step of manipulating the valve so that fluid positioned within the gravity-drain collection container flows into the suction-drain collection container.

\* \* \* \* \*